(12) United States Patent
Weinstein

(10) Patent No.: US 10,539,442 B2
(45) Date of Patent: Jan. 21, 2020

(54) FLUID MOMENTUM DETECTION METHOD AND RELATED APPARATUS

(71) Applicant: Micro Motion, Inc., Boulder, CO (US)

(72) Inventor: Joel Weinstein, Boulder, CO (US)

(73) Assignee: Micro Motion, Inc., Boulder, CO (US)

( * ) Notice: Subject to any disclaimer, the term of this patent is extended or adjusted under 35 U.S.C. 154(b) by 245 days.

(21) Appl. No.: 15/316,966

(22) PCT Filed: Jul. 1, 2014

(86) PCT No.: PCT/US2014/045108
§ 371 (c)(1),
(2) Date: Dec. 7, 2016

(87) PCT Pub. No.: WO2016/003447
PCT Pub. Date: Jan. 7, 2016

(65) Prior Publication Data
US 2017/0115142 A1    Apr. 27, 2017

(51) Int. Cl.
*G01F 1/20* (2006.01)
*G01N 9/00* (2006.01)
*G01F 1/86* (2006.01)
*G01F 1/84* (2006.01)

(52) U.S. Cl.
CPC .......... *G01F 1/206* (2013.01); *G01F 1/8463* (2013.01); *G01F 1/8468* (2013.01); *G01F 1/86* (2013.01); *G01N 9/002* (2013.01)

(58) Field of Classification Search
CPC ... G01F 1/206; G01F 1/80; G01F 1/86; G01F 1/00; G01F 1/8463; G01F 1/8468; G01N 9/002
See application file for complete search history.

(56) References Cited

U.S. PATENT DOCUMENTS

| 3,340,733 A | * | 9/1967 | Lasher | ...................... | G01F 1/00 |
| | | | | | 73/861.74 |
| 3,945,109 A | * | 3/1976 | Leftheris | ................ | B21D 26/14 |
| | | | | | 29/525 |
| 5,033,313 A | | 7/1991 | Lew | | |
| 6,684,715 B1 | | 2/2004 | Cage | | |
| 2007/0193371 A1 | | 8/2007 | Yamane et al. | | |

FOREIGN PATENT DOCUMENTS

JP    H07311064 A    11/1995
WO    2006104485 A1    10/2006

* cited by examiner

*Primary Examiner* — Matthew G Marini
(74) *Attorney, Agent, or Firm* — The Ollila Law Group LLC

(57) ABSTRACT

A method is provided for determining fluid momentum through one or more conduits. The method comprises the step of receiving an elongation signal from an elongation sensor indicating an elongation of the one or more conduits due to the flowing fluid. A momentum term is then calculated.

14 Claims, 9 Drawing Sheets

FLUID MOMENTUM DETECTION METHOD AND RELATED APPARATUS

FIELD OF THE INVENTION

The embodiments described below relate to the field of fluid flow, and more particularly, to an improved fluid momentum detection method and related apparatus.

BACKGROUND

Vibrating conduit sensors, such as Coriolis mass flowmeters and vibrating densitometers, typically operate by detecting motion of a vibrating conduit that contains a flowing material. Properties associated with the material in the conduit, such as mass flow, density and the like, can be determined by processing measurement signals received from motion transducers associated with the conduit. The vibration modes of the vibrating material-filled system generally are affected by the combined mass, stiffness, and damping characteristics of the conduit and the material contained therein.

It is well known to use vibrating flowmeters to measure mass flow and other properties of materials flowing through a pipeline. For example, vibrating Coriolis flowmeters are disclosed in U.S. Pat. No. 4,491,025 issued to J. E. Smith, et al. and also Re. 31,450 to J. E. Smith. These flowmeters have one or more fluid tubes (or "flow tubes"). Each flow tube configuration in a Coriolis mass flowmeter has a set of natural vibration modes, which may be of a simple bending, torsional, radial, lateral, or coupled type. Each flow tube is driven to oscillate at resonance in one of these natural modes. The vibration modes are generally affected by the combined mass, stiffness, and damping characteristics of the flow tube and the material contained therein, thus mass, stiffness, and damping are typically determined during an initial calibration of the flowmeter using well-known techniques.

Material flows into the flowmeter from a connected pipeline on the inlet side of the flowmeter. The material is then directed through the flow tube or flow tubes and exits the flowmeter to a pipeline connected on the outlet side.

A driver, such as a voice-coil style driver, applies a force to the one or more flow tubes. The force causes the one or more flow tubes to oscillate. When there is no material flowing through the flowmeter, all points along a flow tube oscillate with an identical phase. As a material begins to flow through the flow tubes, Coriolis accelerations cause each point along the flow tubes to have a different phase with respect to other points along the flow tubes. The phase on the inlet side of the flow tube lags the driver, while the phase on the outlet side leads the driver. Sensors are typically placed at two different points on the flow tube to produce sinusoidal signals representative of the motion of the flow tube at the two points. A phase difference of the two signals received from the sensors is calculated in units of time.

The phase difference between the two sensor signals is proportional to the mass flow rate of the material flowing through the flow tube or flow tubes. The mass flow rate of the material is determined by multiplying the phase difference by a flow calibration factor. The flow calibration factor is dependent upon material properties and cross-sectional properties of the flow tube. One of the major characteristics of the flow tube that affects the flow calibration factor is the flow tube's stiffness. Prior to installation of the flowmeter into a pipeline, the flow calibration factor is determined by a calibration process. In the calibration process, a fluid is passed through the flow tube at a given flow rate and the proportion between the phase difference and the flow rate is calculated. The flow tube's stiffness and damping characteristics are also determined during the calibration process as is generally known in the art.

One advantage of a Coriolis flowmeter is that the accuracy of the measured mass flow rate is largely not affected by wear of moving components in the flowmeter, as there are no moving components in the vibrating flow tube. The flow rate is determined by multiplying the phase difference between two points on the flow tube and the flow calibration factor. The only input is the sinusoidal signals from the sensors indicating the oscillation of two points on the flow tube. The phase difference is calculated from the sinusoidal signals. Since the flow calibration factor is proportional to the material and cross-sectional properties of the flow tube, the phase difference measurement and the flow calibration factor are not affected by wear of moving components in the flowmeter.

A typical Coriolis mass flowmeter includes one or more transducers (or pickoff sensors, or simply "pickoffs"), which are typically employed in order to measure a vibrational response of the flow conduit or conduits, and are typically located at positions upstream and downstream of the driver. The pickoffs are connected to electronic instrumentation. The instrumentation receives signals from the two pickoffs and processes the signals in order to derive a mass flow rate measurement, among other things.

Typical Coriolis flowmeters measure flow and/or density through the use of a coil and magnet as a pickoff to measure the motion of a meter's vibrating flow tube/tubes. The mass flow rate through the meter is determined from the phase difference between multiple pickoff signals located near the inlet and outlet of the meter's flow tubes. However, it is possible to measure flow using strain gages in place of coil/magnet pickoffs. A fundamental difference between the two sensor types is that coil/magnet pickoffs measure the velocity of the flow tubes and strain gages measure the strain of the flow tubes which is proportional to the tubes' displacement. As such, the placement of each type of sensor will not necessarily be in the same location.

Strain gages have a number of advantages over coil/magnet pickoffs. Strain gages are cheaper to produce and implement than coil/magnet pickoffs. They also help to eliminate point masses that may adversely affect system operation. Additionally, strain gages do not need a reference point from where to measure strain like coil/magnet pickoffs. This allows for single flow tube designs that are not possible with coil/magnet pickoffs.

Momentum conservation, according to the conservation of momentum principle, requires that the momentum over a given time remain unchanged as steady flow occurs through an isolated system of fluid, such as through the flow tube of a vibratory flowmeter. Since momentum is a vector quantity, a change in direction of the flow causes a reduction of momentum in the original direction which is offset by an increase in the new direction. Fluid travelling through a bend in a pipe, for example, exerts a force on the pipe which must be counteracted by an anchor force to prevent the pipe from moving. This is the reason thrust blocks are often installed proximate pipe bends in municipal water pipe systems, for example.

In the case of a U-bend, such as is often found in the flow tubes of vibratory flowmeters, the fluid that enters the flow tubes is redirected 180° so return flow travels back in the same direction from which the fluid entered the flow tubes.

This change in direction causes the flow to exert two axial y-direction forces on the flow tube: internal pressure and a momentum re-direction.

The embodiments described below provide means to measure fluid momentum. It is an object to provide an embodiment for the measurement of fluid momentum in a pipeline. It is an object to provide an embodiment for the measurement of fluid momentum in a vibratory meter. It is an object to provide an embodiment for the measurement of fluid momentum to detect pipe coating or plugging in a pipeline. It is an object to provide an embodiment for the detection of pipe coating or plugging in a vibratory meter. It is an object to calculate mass and volume flow rate in a vibrating meter using the measurement of fluid momentum.

SUMMARY OF THE INVENTION

A method for determining fluid momentum through one or more conduits is provided according to an embodiment. The method comprises the steps of receiving an elongation signal from an elongation sensor indicating an elongation of the one or more conduits due to a flowing fluid, and calculating a momentum term.

A flowmeter including a sensor assembly and a meter electronics is provided according to an embodiment. According to an embodiment, the flowmeter comprises one or more flow tubes and a driver coupled to the one or more flow tubes that is oriented to induce a drive mode vibration in the one or more flow tubes. At least two pickoffs are coupled to the one or more flow tubes and configured to detect the drive mode vibration. One or more elongation sensors are coupled to the one or more flow tubes, wherein the one or more elongation sensors are configured to output a signal whose amplitude is proportional to a fluid momentum-induced strain of the one or more flow tubes, and wherein the meter electronics is configured to calculate a momentum term.

Aspects

According to an aspect, a method for determining fluid momentum through one or more conduits, comprises the steps of: receiving an elongation signal from an elongation sensor indicating an elongation of the one or more conduits due to a flowing fluid, and calculating a momentum term.

Preferably, calculating the momentum term comprises the step of deriving the momentum term from an axial strain equation comprising $$\varepsilon_y = \frac{-F_{Ay}}{A_t E} = \frac{+2mv + 2Ap_{avg}}{A_t E},$$

wherein:
mv is the momentum term;
$\varepsilon_y$ is the axial strain of the one or more conduits;
$F_{Ay}$ is an anchor force of the one or more conduits;
$A_t$ is a cross-sectional area of the one or more conduits;
E is a modulus of elasticity of the one or more conduits;
m is a mass flow rate of the fluid;
v is a fluid velocity of the fluid;
A is a cross-sectional area of the fluid; and
$p_{avg}$ is an average static pressure of the fluid.

Preferably, the method for determining fluid momentum through one or more conduits comprises the steps of: receiving a temperature signal from a temperature sensor, and calculating a temperature-corrected momentum term.

Preferably, calculating a temperature-corrected momentum term comprises the step of deriving a temperature-corrected momentum term from an axial strain equation comprising $$\varepsilon_y = \frac{-F_{Ay}}{A_t E} = \frac{+2mv + 2Ap_{avg}}{A_t E} + \alpha_T \Delta T,$$

wherein:
$F_{Ay}$ is an anchor force;
mv is the momentum term;
$\varepsilon_y$ is the axial strain of the one or more conduits;
$A_t$ is a cross-sectional area of the one or more conduits;
E is a modulus of elasticity of the one or more conduits;
m is a mass flow rate of the fluid;
v is a fluid velocity of the fluid;
A is a cross-sectional area of the fluid;
$p_{avg}$ is an average static pressure of the fluid;
$\alpha_T$ is a coefficient of linear thermal expansion of the one or more conduits; and
$\Delta T$ is a change in a temperature of the one or more conduits.

Preferably, the one or more conduits comprise one or more flow tubes of a vibratory flowmeter.

Preferably, the method for determining fluid momentum through one or more conduits comprises the steps of: vibrating at least one of the one or more flow tubes in a drive mode vibration; providing a first pickoff and a second pickoff on at least one of the one or more flow tubes; receiving a first pickoff signal and second pickoff signal from the first pickoff and the second pickoff, respectively, based on a vibrational response to the drive mode vibration; calculating a difference between the first pickoff signal and second pickoff signal; determining a mass flow from the pickoff signal difference; and comparing the mass flow with the momentum term.

Preferably, the step of comparing the mass flow with the momentum term comprises calculating a velocity, v, comprising m=ρAv, wherein:
m is the mass flow rate of the fluid;
ρ is a density of the fluid; and
A is a cross-sectional area of the fluid; and
calculating a calculated momentum product term by multiplying the velocity and the mass flow rate; comparing the calculated momentum product term with the momentum term; and indicating a fault if the calculated momentum product term deviates from the momentum term to a degree greater than a predetermined threshold.

Preferably, the step of providing an elongation sensor on the one or more conduits proximate a conduit region subjected to momentum re-direction forces, comprises the steps of: receiving a first and second elongation sensor signal from a first and a second elongation sensor, respectively, based on vibrational responses to the drive mode vibrations; calculating a first momentum term from the first elongation sensor signal, and a second momentum term from the second elongation sensor signal; comparing the first momentum term to the second momentum term; and determining the presence of a flow asymmetry between the first and second flow tubes.

Preferably, the method for determining fluid momentum through one or more conduits comprises the step of indicating a presence of a flow asymmetry if the difference in the first momentum term and second momentum term is greater than a predetermined threshold.

Preferably, the method for determining fluid momentum through one or more conduits comprises the steps of calculating a mass flow rate and volume flow rate with a density of the fluid and the momentum term.

Preferably, the step of providing a density of the fluid comprises the step of measuring the density of the fluid.

According to an aspect, a flowmeter including a sensor assembly and a meter electronics, comprises: one or more flow tubes; a driver coupled to the one or more flow tubes and oriented to induce a drive mode vibration in the one or more flow tubes; at least two pickoffs coupled to the one or more flow tubes and configured to detect the drive mode vibration; and one or more elongation sensors coupled to the one or more flow tubes, wherein the one or more elongation sensors are configured to output a signal whose amplitude is proportional to a fluid momentum-induced strain of the one or more flow tubes, and wherein the meter electronics is configured to calculate a momentum term.

Preferably, the momentum term is derived from an axial strain equation comprising $$\varepsilon_y = \frac{-F_{Ay}}{A_t E} = \frac{+2mv + 2Ap_{avg}}{A_t E},$$

wherein:
mv is the momentum term;
$\varepsilon_y$ is the axial strain of the conduit;
$F_{Ay}$ is an anchor force of the conduit;
$A_t$ is a cross-sectional area of the conduit;
E is a modulus of elasticity of the conduit;
m is a mass flow rate of the fluid;
v is a fluid velocity of the fluid;
A is a cross-sectional area of the fluid; and
$p_{avg}$ is an average static pressure of the fluid.

Preferably, at least one temperature sensor is coupled to the one or more flow tubes, wherein the meter electronics is configured to calculate a temperature-corrected momentum term.

Preferably, the temperature-corrected momentum is derived from an axial strain equation comprising $$\varepsilon_y = \frac{-F_{Ay}}{A_t E} = \frac{+2mv + 2Ap_{avg}}{A_t E} + \alpha_T \Delta T,$$

wherein:
$F_{Ay}$ is an anchor force;
mv is the momentum term;
$\varepsilon_y$ is the axial strain of the conduit;
$A_t$ is a cross-sectional area of the conduit;
E is a modulus of elasticity of the conduit;
m is a mass flow rate of the fluid;
v is a fluid velocity of the fluid;
A is a cross-sectional area of the fluid;
$p_{avg}$ is an average static pressure of the fluid;
$\alpha_T$ is a coefficient of linear thermal expansion of the conduit; and
$\Delta T$ is a change in the conduit temperature.

Preferably, the elongation sensor comprises at least one of a strain gage, an optical sensor, and a laser.

Preferably, the one or more flow tubes comprise at least one of a 180° U-bend and an omega-shaped bend.

Preferably, the signal is a resistance having an amplitude proportional to the fluid momentum-induced strain.

Preferably, the one or more elongation sensors coupled to the one or more flow tubes comprises a first elongation sensor coupled to a first flow tube of the one or more flow tubes and a second elongation sensor coupled to a second flow tube of the one or more flow tubes.

Preferably, the meter electronics is configured to detect a flow asymmetry between the first and second flow tubes.

BRIEF DESCRIPTION OF THE DRAWINGS

The same reference number represents the same element on all drawings. The drawings are not necessarily to scale.

DETAILED DESCRIPTION OF THE INVENTION

FIGS. 1-10 and the following description depict specific examples to teach those skilled in the art how to make and use the best mode of embodiments of a method for detecting fluid momentum and a related apparatus. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 1:
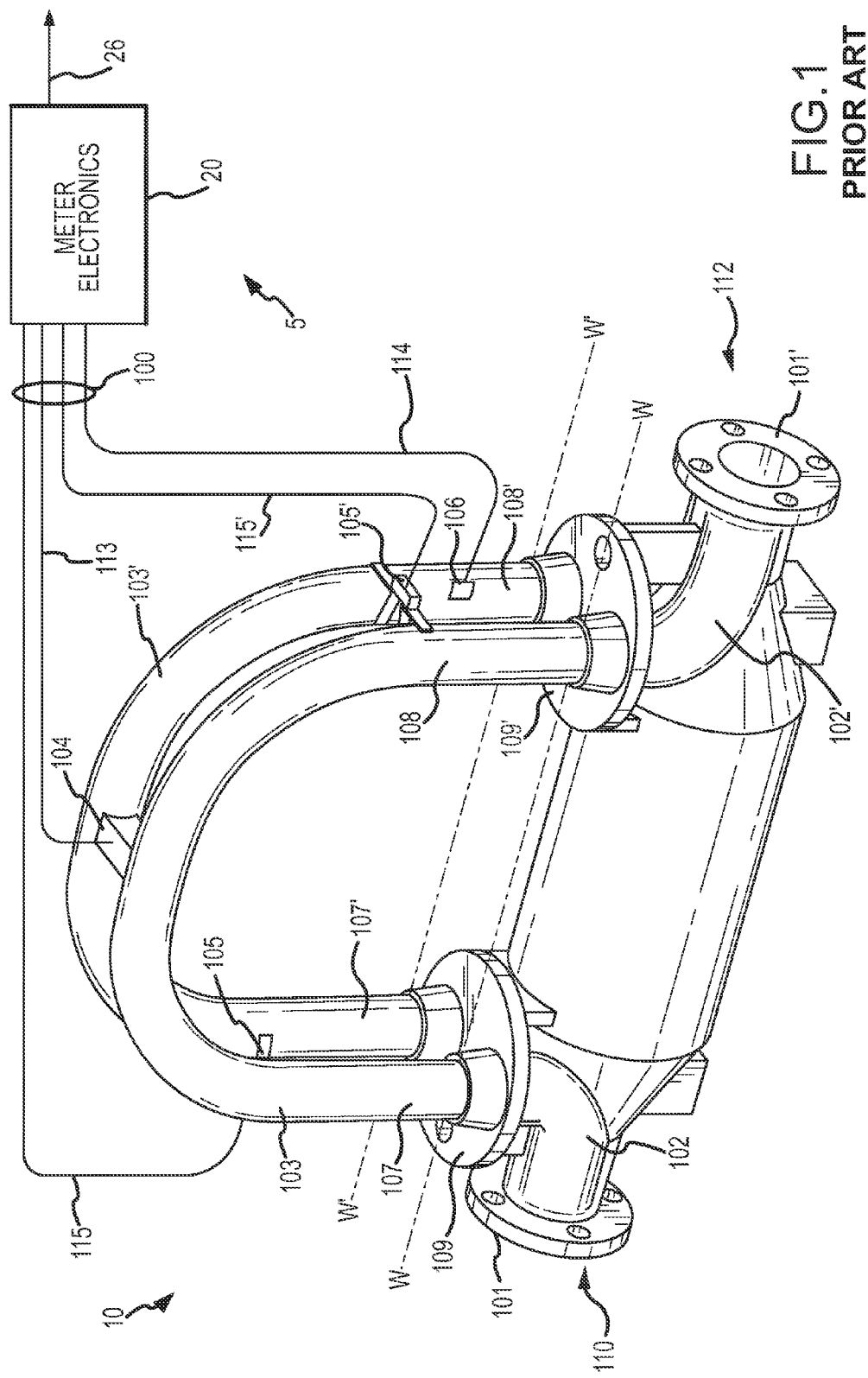
FIG. 1 illustrates a prior art flowmeter.

FIG. 1 illustrates a prior art flowmeter 5, which can be any vibrating meter, such as a Coriolis flowmeter. The flowmeter 5 comprises a sensor assembly 10 and meter electronics 20. The sensor assembly 10 responds to mass flow rate and density of a process material. Meter electronics 20 are connected to the sensor assembly 10 via leads 100 to provide density, mass flow rate, and temperature information over path 26, as well as other information not relevant to the present invention. Sensor assembly 10 includes flanges 101 and 101', a pair of manifolds 102 and 102', a pair of parallel flow tubes 103 (first flow tube) and 103' (second flow tube), a driver 104, a temperature sensor 106 such as a resistive temperature detector (RTD), and a pair of pickoffs 105 and 105', such as magnet/coil pickoffs, strain gages, optical sensors, or any other pickoff known in the art. The flow tubes 103 and 103' have inlet legs 107 and 107' and outlet legs 108 and 108', respectively. Flow tubes 103 and 103' bend at least one symmetrical location along their length and are essentially parallel throughout their length. Each flow tube 103, 103', oscillate about axes W and W', respectively.

The legs 107, 107', 108, 108' of flow tubes 103,103' are fixedly attached to flow tube mounting blocks 109 and 109' and these blocks, in turn, are fixedly attached to manifolds 102 and 102'. This provides a continuous closed material path through the sensor assembly 10.

When flanges 101 and 101' are connected to a process line (not shown) that carries the process material that is being measured, material enters a first end 110 of the flowmeter 5 through a first orifice (not visible in the view of FIG. 1) in flange 101 and is conducted through the manifold 102 to flow tube mounting block 109. Within the manifold 102, the material is divided and routed through flow tubes 103 and 103'. Upon exiting flow tubes 103 and 103', the process material is recombined in a single stream within manifold 102' and is thereafter routed to exit a second end 112 connected by flange 101' to the process line (not shown).

Flow tubes 103 and 103' are selected and appropriately mounted to the flow tube mounting blocks 109 and 109' so as to have substantially the same mass distribution, moments of inertia, and Young's modulus about bending axes W-W and W'-W', respectively. Inasmuch as the Young's modulus of the flow tubes 103, 103' changes with temperature, and this change affects the calculation of flow and density, a temperature sensor 106 is mounted to a flow tube 103, 103' to continuously measure the temperature of the flow tube. The temperature of the flow tube, and hence the voltage appearing across the temperature sensor 106 for a given current passing therethrough, is governed primarily by the temperature of the material passing through the flow tube. The temperature-dependent voltage appearing across the temperature sensor 106 is used in a well-known method by meter electronics 20 to compensate for the change in elastic modulus of flow tubes 103, 103' due to any changes in flow tube temperature. The temperature sensor is connected to meter electronics 20.

Both flow tubes 103, 103' are driven by driver 104 in opposite directions about their respective bending axes W and W' at what is termed the first out-of-phase bending mode of the flowmeter. This driver 104 may comprise any one of many well-known arrangements, such as a magnet mounted to flow tube 103' and an opposing coil mounted to flow tube 103, through which an alternating current is passed for vibrating both flow tubes. A suitable drive signal is applied by meter electronics 20, via lead 113, to the driver 104.

Meter electronics 20 receive the temperature signal on lead 114, and the left and right velocity signals appearing on leads 115 and 115', respectively. Meter electronics 20 produce the drive signal appearing on lead 113 to driver 104 and vibrate flow tubes 103, 103'. Meter electronics 20 processes the left and right velocity signals and the temperature signal to compute the mass flow rate and the density of the material passing through sensor assembly 10. This information, along with other information, is applied by meter electronics 20 over path 26 to utilization means.

Figure 2:
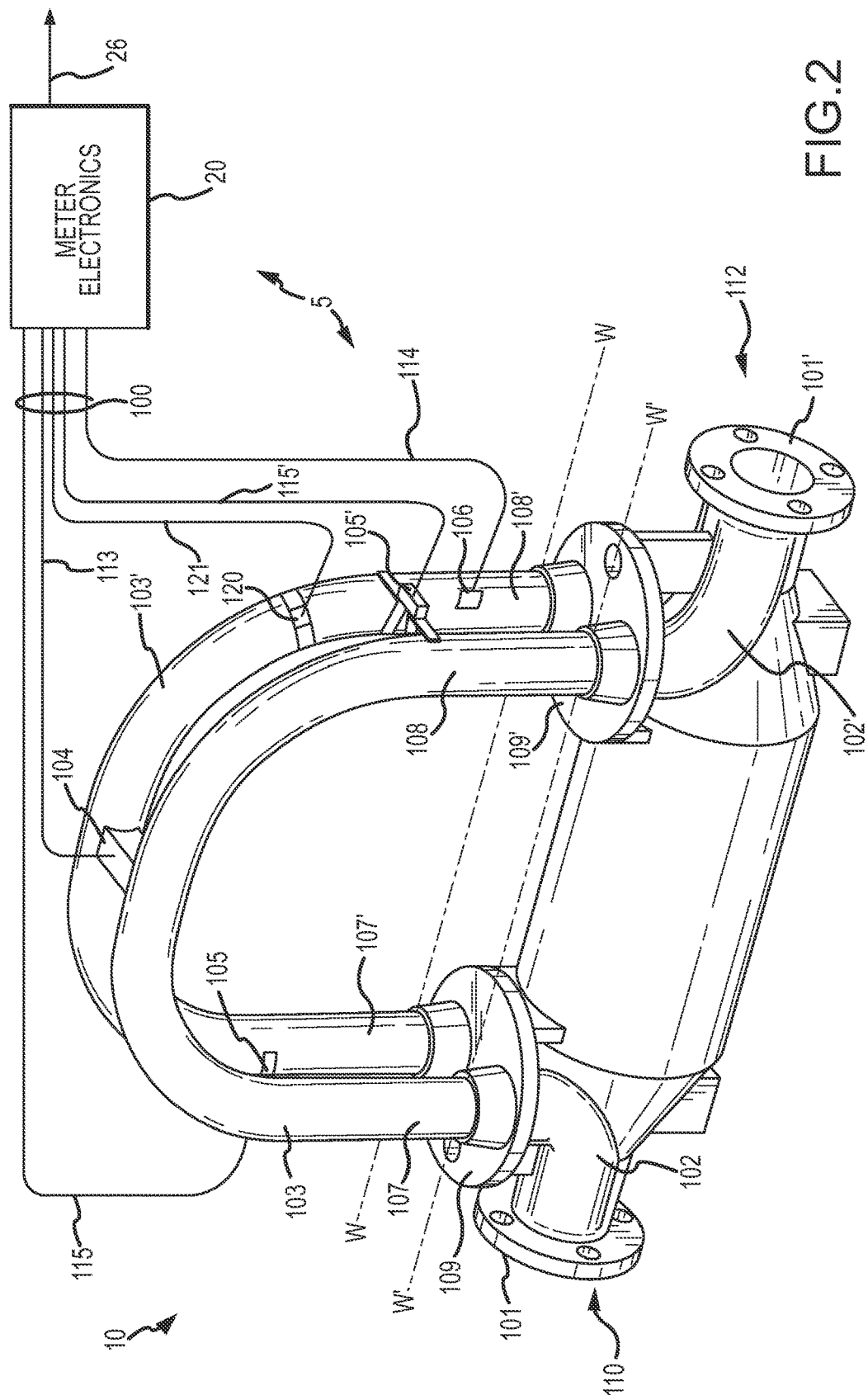
FIG. 2 illustrates an embodiment of a flowmeter.

FIG. 2 illustrates an embodiment of a flowmeter 5. A Coriolis flowmeter structure is described although it is apparent to those skilled in the art that the present invention could be practiced as a vibrating tube densitometer without the additional measurement capability provided by a Coriolis mass flowmeter. In fact, the present invention may be utilized in pipelines of all sizes, with or without means for measuring mass flow, density, etc. Common elements with the prior art device of FIG. 1 share the same reference numbers.

The flow tubes 103 and 103' are driven by driver 104 in opposite directions about their respective bending axes W and W' and at what is termed the first out-of-phase bending mode of the flowmeter. This driver 104 may comprise any one of many well-known arrangements, such as a magnet mounted to flow tube 103' and an opposing coil mounted to flow tube 103 and through which an alternating current is passed for vibrating both flow tubes. It should be noted that the flow tubes 103, 103' are substantially rigid—made from a metal, for example—such that they are capable of only limited motion, such as, for example, the vibratory motion induced by a driver. A suitable drive signal is applied by meter electronics 20, via lead 113, to the driver 104.

As a fluid courses through a pipe or flow tube (henceforth referred to only as flow tube) that exhibits a 180° U-bend, the fluid is re-directed back in the same direction from which it entered the flow tube. A 180° U-bend is merely an example of a configuration contemplated. Other shapes and degrees of bend are contemplated to be within the scope of the description and claims. The flow tube therefore experiences two axial y-direction forces due to fluid momentum, namely an internal pressure and a momentum re-direction. Summing the forces on the fluid control volume equates to an anchor force in a y-direction as shown in Equation (1):

$$F_{Ay} = -m(v_1+v_2) - A_1 p_1 - A_2 p_2 \qquad (1)$$

Where:
m=mass flow rate
v=fluid velocity
A=cross-sectional area of the fluid
p=static pressure The minus signs in Equation (1) indicate that the direction of the force required to maintain the flow tube in a stationary position are in the negative y-direction. It should be noted that in many cases an x-axis component would be present, such as for a 90° bend in a flow tube, as there would be a force component also acting in the x-direction. Since, the flow tube in the instant case has a symmetric bend (e.g. 180° U-bend), the x-direction forces cancel out.

As is indicated in Equation (1), the reaction force due to fluid momentum change, $-m(v_1+v_2)$, causes the flow tube to elongate in the y-direction. The pressure forces will also cause the flow tube to elongate in the y-direction, but will also radially strain the flow tube. The magnitude of the y-direction elongation can be predicted using a negative anchor force, $F_{Ay}$, to indicate the force exerted by the fluid, as is exemplified by Equations (2) and (3):

$$\sigma_y = \frac{-F_{Ay}}{A_t} \qquad (2)$$

$$\sigma_y = E\varepsilon_y \qquad (3)$$

Where:
$\sigma_y$=axial stress
$A_t$=cross-sectional area of flow tube
E=modulus of elasticity
$\varepsilon_y$=axial strain By combining Equations (2) and (3), an expression is derived for axial strain in terms of the fluid anchor force required due to the pressure and momentum terms, as is shown by Equation (4).

$$\varepsilon_y = \frac{-F_{Ay}}{A_t E} = \frac{m(v_1+v_2) + A_1 p_1 + A_2 p_2}{A_t E} \qquad (4)$$

Applying the above equation to an embodiment of a flowmeter 5, constant cross-sectional geometry is applied, thus $A_1=A_2$. A linear drop in pressure throughout the flow tube is also assumed, so a simplified equation, Equation (5), is derived:

$$\varepsilon_y = \frac{-F_{Ay}}{A_t E} = \frac{+2mv + 2Ap_{avg}}{A_t E} \quad (5)$$

Where:

$P_{avg}$=average pressure in flow tube

Figure 3:
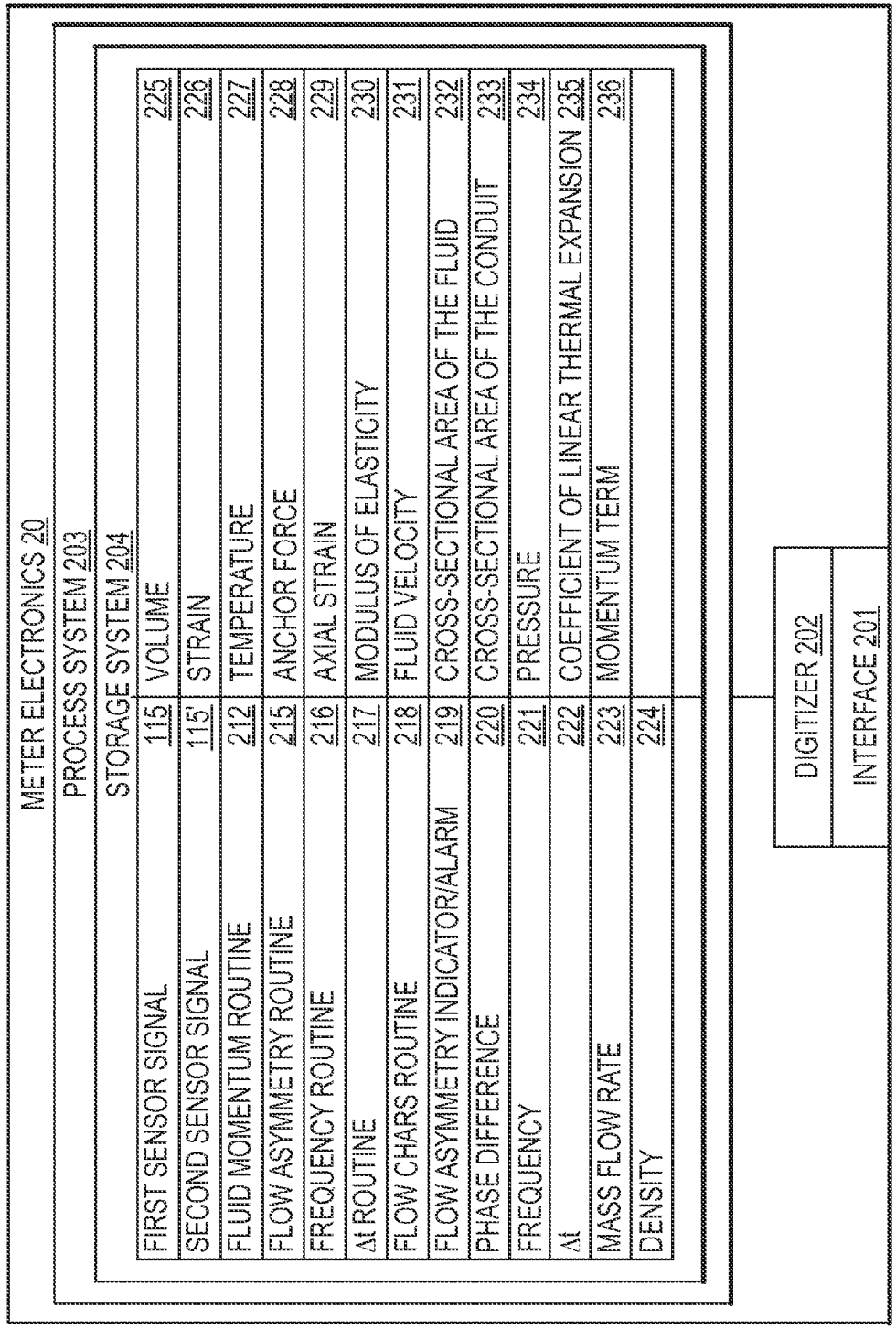
FIG. 3 is a diagram of meter electronics.

FIG. 3 illustrates meter electronics 20 of the flowmeter 5 according to an embodiment of the invention. The meter electronics 20 can include an interface 201 and a processing system 203. The meter electronics 20 receives first and second sensor signals 115, 115' from the sensor assembly 10, such as from pickoffs 105, 105', for example. The meter electronics 20 processes the first and second sensor signals 115, 115' in order to obtain flow characteristics of the flow material flowing through the sensor assembly 10. For example, the meter electronics 20 can determine one or more of a phase difference, a frequency, a time difference (Δt), a density, a mass flow rate, a fluid velocity, a pressure, a temperature, a strain, and a volume flow rate from the sensor signals, for example. In addition, other flow characteristics can be determined according to the invention.

The interface 201 receives the sensor signals from the pickoffs 105, 105' via the leads 100 illustrated in FIG. 2. The interface 201 can perform any necessary or desired signal conditioning, such as any manner of formatting, amplification, buffering, etc. Alternatively, some or all of the signal conditioning can be performed in the processing system 203.

In addition, the interface 201 can enable communications between the meter electronics 20 and external devices, such as through the communication path 26, for example. The interface 201 can be capable of any manner of electronic, optical, or wireless communication.

The interface 201, in one embodiment, includes a digitizer 202, wherein the sensor signal comprises an analog sensor signal. The digitizer samples and digitizes the analog sensor signal and produces a digital sensor signal. The interface/digitizer can also perform any needed decimation, wherein the digital sensor signal is decimated in order to reduce the amount of signal processing needed and to reduce the processing time.

The processing system 203 conducts operations of the meter electronics 20 and processes measurements from the sensor assembly 10. The processing system 203 executes one or more processing routines and thereby processes the measurements in order to produce one or more characteristics.

The processing system 203 can comprise a general purpose computer, a microprocessing system, a logic circuit, or some other general purpose or customized processing device. The processing system 203 can be distributed among multiple processing devices. The processing system 203 can include any manner of integral or independent electronic storage medium, such as the storage system 204.

In the embodiment illustrated, the processing system 203 determines the flow characteristics from signals derived from at least pickoffs 105, 105', a temperature sensor 106, and an elongation sensor 120. The processing system 203 can determine at least a magnitude, strain, phase difference, time difference, and a frequency of the two or more responses from pickoffs 105, 105'. In an embodiment, a pickoff 105, 105' and/or an elongation sensor 120 comprise a strain gage. Voltage from at least one bridge circuit (not shown) such as a Wheatstone bridge circuit in electrical communication with at least one strain gage, is input into the meter electronics 20. In an embodiment, only a single bridge circuit is present, and in other embodiments, at least two bridge circuits are present.

The storage system 204 can store flowmeter parameters and data, software routines, constant values, and variable values. In one embodiment, the storage system 204 includes routines that are executed by the processing system 203. In one embodiment, the storage system 204 stores a fluid momentum routine 212, a flow asymmetry routine 215, a frequency routine 216, a time difference (Δt) routine 217, a flow characteristics routine 218, and a flow asymmetry alarm flag and/or routine 219.

In one embodiment, the storage system 204 stores variables used to operate the flowmeter 5. The storage system 204 in one embodiment stores variables such as vibrational responses 220, 221, 222, 226 which are received/derived from the pickoffs 105, 105'. Any routine with meter electronics 20 may utilize variables such as, for example without limitation, phase difference 220, frequency 221, time delay 222, mass flow rate 223, density 224, volume 225, strain 226, and temperature 227. Strain 226 may also be received from the elongation sensor 120 in some embodiments. Other variables may include, for example without limitation, anchor force 228, axial strain 229, modulus of elasticity 230, fluid velocity 231, cross-sectional area of the fluid 232, cross-sectional area of the conduit 233, pressure 234, coefficient of linear thermal expansion 235, and a momentum term 236. In some embodiments, the storage system 204 stores one or more values generated by the meter electronics 20. In some embodiments, the storage system 204 stores one or more flow characteristics obtained from the sensor measurements. In some embodiments, the storage system 204 stores one or more constant variables.

Embodiments sense flow by directly measuring the relative motion of the outlet 108, 108' (or inlet 107, 107') side of a flow tube 103, 103' with respect to the inlet 107, 107' (or outlet 108, 108') side of the same flow tube 103, 103'. In embodiments where strain gages are employed as pickoffs 105, 105', they may be connected to at least one bridge circuit, and are configured to produce a zero-amplitude signal during a no flow condition (which corresponds to a normal mode shape of the drive mode, i.e. no phase between inlet and outlet of the tubes). During flow, the same configuration will produce a sinusoid signal output whose amplitude is a function of flow rate (which corresponds to the mode shape gaining complexity, i.e. inlet/outlet phase, due to flow). In related embodiments, combined signals from one or more strain gages on the inlet side of a meter and the combined signals from one or more strain gages on the outlet side of the meter are input into the meter electronics 20. These signals are then treated like coil/magnet pickoff signals, wherein a phase measurement is derived from the inlet and outlet signals. Bridge circuits may be used in these embodiments for amplifying the signal. In other embodiments, however, strain signals from the inlet and outlet portions of the flow tubes 103, 103', are combined in a bridge circuit. In this case, there is only one signal input into the meter electronics whose amplitude is proportional to phase.

A bridge circuit converts small changes in the resistance of a strain gage into relatively large changes in voltage. The bridge circuit comprises a supply voltage, $V_s$, four resistors ($R_1$ through $R_4$), and an output voltage, $V_o$. The bridge circuit is considered balanced, and the output voltage is 0 volts when $R_1=R_2$ and $R_3=R_4$. A change in any of the resistors will unbalance the bridge and the output voltage will no longer be zero. The relationship between the supply voltage, resistances, and output voltage is shown in Equation (6).

$$V_o = \left(\frac{R_3}{R_3-R_4} - \frac{R_2}{R_1-R_2}\right) * V_s \qquad (6)$$

Any or all of the resistors in the bridge circuit can be replaced by a strain gage. The above equation serves merely as an example, and other equations or algorithms are contemplated herein.

In an embodiment, a first strain gage pickoff 105 is located on inlet leg 107 of the first flow tube 103 and a second strain gage pickoff 105' is located on the outlet leg 108 of the first flow tube 103. The primary difference between coil/magnet pickoffs and strain gages is that coil/magnet pickoffs measure the velocity of the flow tubes and strain gages measure the strain of the flow tubes. Each strain gage disclosed herein may be oriented to detect strain that is induced by a flow tube's 103, 103' drive mode motion. In an embodiment, the strain gages are oriented substantially parallel to a longitudinal axis of the flow tube to which that strain gage is coupled.

For pickoffs 105, 105' of the coil/magnet variety, the maximal velocity amplitude is proximate the driver 104, which is typically located in the center of the "U" of a flow tube 103, 103'. However, coil/magnet type pickoffs 105, 105' are not placed in this location as this would place the pickoffs too close to the driver 104, so they are rather located at an area that provides suboptimal, yet resolvable, velocity amplitude to detect a phase signal differential. Maximum strain amplitude, however, is proximate a distal region of the flow tube's 103, 103' inlet/outlet legs 107, 107', 108, 108', and this is where the strain gages may be located in the embodiments disclosed herein, however other strain gage locations are contemplated. In the above embodiment two strain gages are noted, but additional strain gages are also contemplated. It should be noted that when a strain gage is utilized as an elongation sensor 120, placement, in an embodiment, is proximate a flow tube 103, 103' region subjected to momentum re-direction forces. One example is placement proximate a straight portion of the flow tubes 103, 103'. In another example, a strain gage is positioned proximate the apex of a curve on a U-shaped or omega-shaped flow tube 103, 103'. In other embodiments, however, an elongation sensor may be placed on or proximate a flow tube mounting block 109, 109'.

Figure 4:
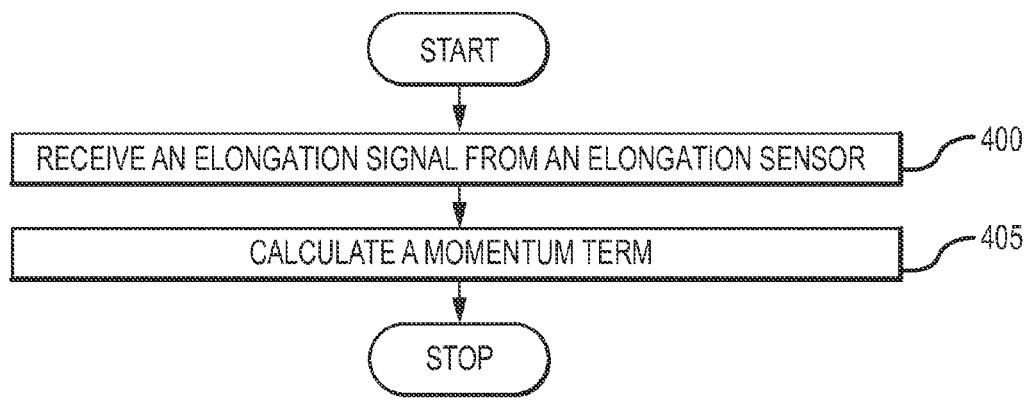
FIG. 4 is a flowchart illustrating an embodiment of a method to calculate a momentum term.

FIG. 4 is a flow chart illustrating a routine performed according to an embodiment, such as a fluid momentum routine 212 or flow characteristics routine 218, for example. This routine outlines a method for determining fluid momentum through one or more conduits. An elongation sensor 120 may be provided on one or more conduits. In an embodiment, the elongation sensor 120 comprises at least one of a strain gage, optical sensor, and a laser. The elongation sensor 120 may be placed proximate a conduit region subjected to momentum re-direction forces. In an embodiment, such as for relatively large oil or water pipeline, for example without limitation, the region subjected to momentum re-direction forces could comprise an expansion joint. In another embodiment, such as for a flowmeter 5, as an example without limitation, a region subjected to measurable momentum re-direction forces comprises at least one of a 180° U-bend and an omega-shaped bend of the flow tube 103, 103'. The measurement could occur on one or more flow tubes 103, 103'. Other symmetrical flow tube configurations are also contemplated, however. Fluid may be provided through the one or more conduits. The fluid can be a liquid, gas, or any combination of liquid and/or gas and/or solid. An elongation signal is received from an elongation sensor 120 in step 400, indicating an elongation/strain of the one or more conduits due to the flowing fluid. A momentum term is calculated in step 405. The momentum term, my, may, in one embodiment, be derived from the axial strain equation, Equation (5), which comprises:

$$\varepsilon_y = \frac{-F_{Ay}}{A_t E} = \frac{+2mv + 2Ap_{avg}}{A_t E}.$$

This equation serves as an example, and should in no way limit the equations or algorithms utilized to derive the momentum term.

Figure 5:
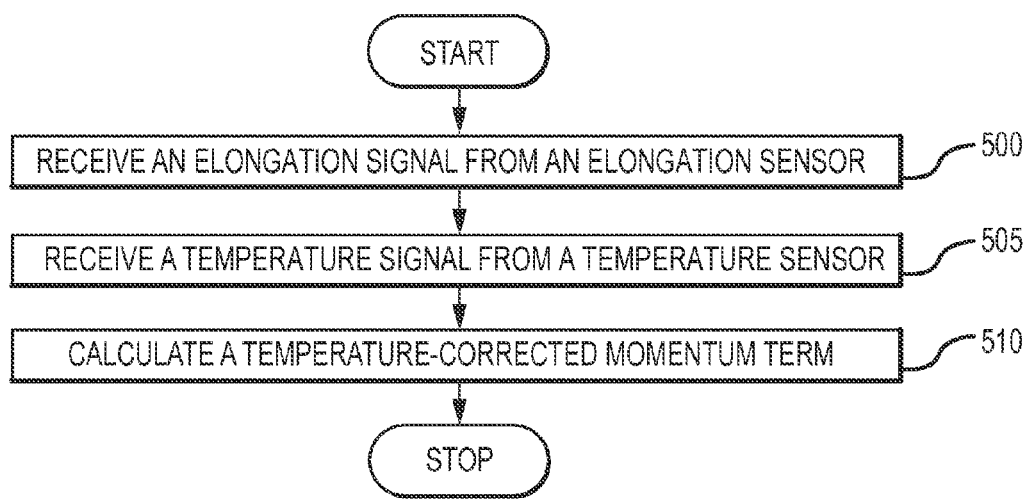
FIG. 5 is a flowchart illustrating an embodiment of a method to calculate a temperature-corrected momentum term.

FIG. 5 is a flow chart illustrating a routine performed according to an embodiment. As in the flow chart of FIG. 4, this routine outlines a method for determining fluid momentum through one or more conduits, but additionally allows for a temperature correction to compensate for thermal expansion. Changes in conduit temperature will cause changes in the conduit's dimensions. In addition, changes in conduit temperature will generally cause a change in the modulus of elasticity of the conduit material, thereby impacting the strain resulting from Equation (5). In order to accurately measure fluid momentum and derive a momentum term, potential temperature-related interference may be considered. To do so, conduit temperature must be accurately measured. An elongation sensor 120 may be provided on one or more conduits, which may be placed proximate a conduit region subjected to momentum re-direction forces. Fluid may be provided through the one or more conduits. An elongation signal is received from an elongation sensor 120 in step 500, indicating an elongation/strain of the one or more conduits due to fluid flow. A temperature sensor 106 may be placed on the one or more conduits. The temperature sensor may be a resistive temperature detector (RTD), but any sensor known in the art is contemplated. A temperature signal is received from a temperature sensor in step 505. A temperature-corrected momentum term is calculated in step 510. The temperature-corrected momentum term may be derived from a modified axial strain Equation (5), comprising:

$$\varepsilon_y = \frac{-F_{Ay}}{A_t E} = \frac{+2mv + 2Ap_{avg}}{A_t E} + \alpha_T \Delta T,$$

wherein $F_{Ay}$ is an anchor force, mv is the temperature-corrected momentum term, $\varepsilon_y$ is the axial strain of the conduit, $A_t$ is a cross-sectional area of the conduit, E is a modulus of elasticity of the conduit at operating temperature, m is a mass flow rate of the fluid, v is a fluid velocity of the fluid, A is a cross-sectional area of the fluid, $p_{avg}$ is an average static pressure of the fluid, $\alpha_T$ is a coefficient of linear thermal expansion of the conduit, and $\Delta T$ is a change in the conduit temperature. This equation serves as an example, and should in no way limit the equations or algorithms utilized to derive the temperature-corrected momentum term.

Figure 6:
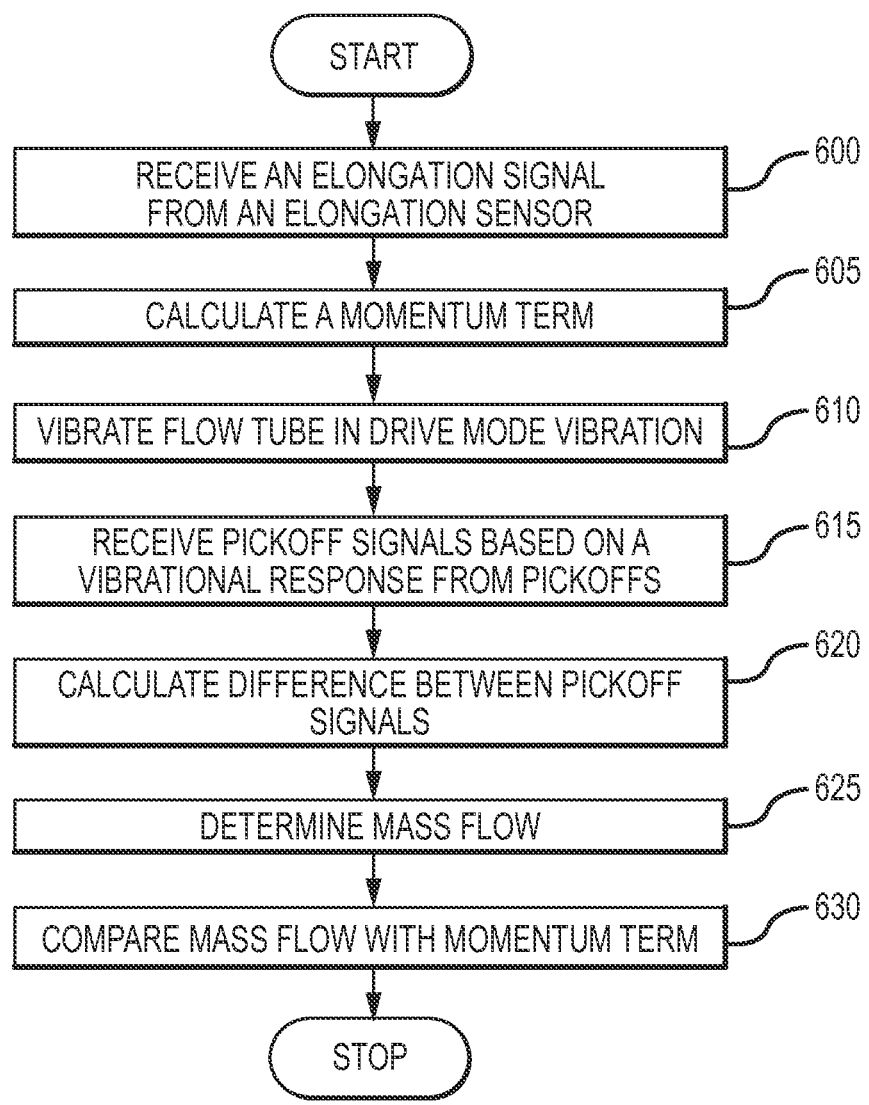
FIG. 6 is a flowchart illustrating an embodiment of a method to calculate a momentum term in a flowmeter.

FIG. 6 is a flow chart illustrating a routine performed according to an embodiment, such as a fluid momentum routine 212, for a flowmeter 5, for example. This routine outlines a method for determining fluid momentum through one or more flow tubes 103, 103', such as those found in a Coriolis mass flowmeter, for example without limitation. An elongation sensor 120 may be provided on one or more flow tubes 103, 103'. The elongation sensor 120 may be placed proximate a flow tube region subjected to momentum re-direction forces, such as the 180° U-bend or omega-shaped bend commonly found on flowmeter flow tubes. Fluid may be provided through the one or more flow tubes 103, 103'. An elongation signal is received from an elongation sensor 120 in step 600, indicating an elongation/strain of the one or more flow tubes 103, 103' to a flowing fluid. A momentum term is calculated in step 605, as described herein. This can be a temperature-corrected momentum term in an embodiment. Two or more pickoffs 105, 105' may be provided for a flow tube 103 or 103'. The one or more flow tubes 103, 103' are vibrated in a drive mode vibration in step 610. In step 615, a first pickoff signal and second pickoff signal, based on a vibrational response to the drive mode vibration from the first pickoff 105 and the second pickoff 105', respectively, are received. A difference between the first pickoff signal and second pickoff signal is calculated in step 620, and a mass flow is determined from the pickoff signal difference in step 625. The meter electronics 20 may then compare the mass flow with the momentum term, as is shown in step 630. For example, if the density of a fluid is known, the momentum term may be used in conjunction with the density for a comparison to the measured mass flow for diagnostic purposes or as a means to measure mass and volume flow rate.

Figure 7:
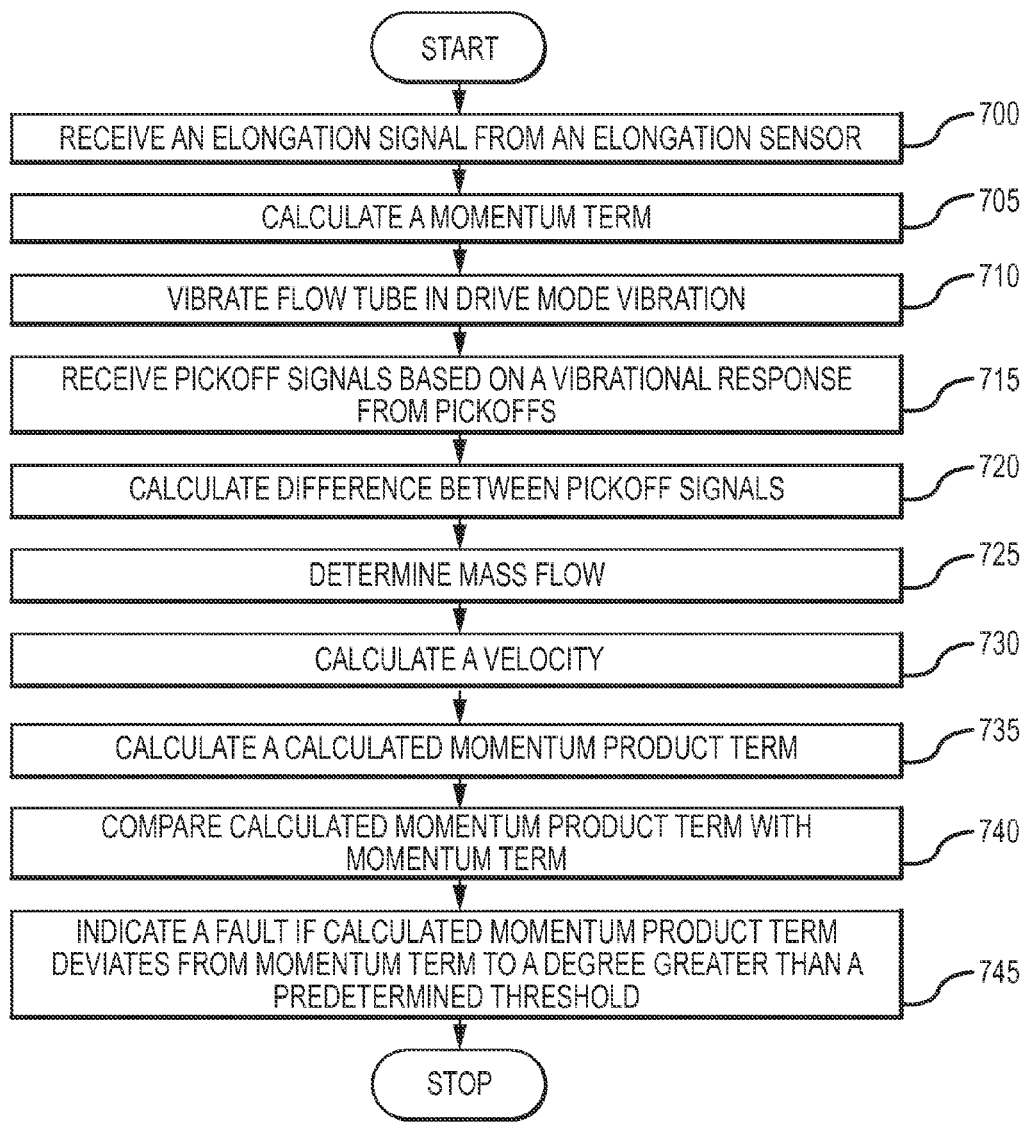
FIG. 7 is a flowchart illustrating an embodiment of a method to calculate a momentum term in a flowmeter and indicate a presence of a measurement fault.

FIG. 7 is a flow chart illustrating a routine performed according to an embodiment to diagnostically check the primary flowmeter 5 measurements using a momentum term. An elongation signal is received from an elongation sensor 120 in step 700, indicating an elongation/strain of the one or more flow tubes 103, 103' to a flowing fluid. A momentum term is calculated in step 705, as described herein. This can be a temperature-corrected momentum term in an embodiment. Two or more pickoffs 105, 105' may be provided for each flow tube 103 or 103'. The one or more flow tubes 103, 103' are vibrated in a drive mode vibration in step 710. In step 715, a first pickoff signal and second pickoff signal, based on a vibrational response to the drive mode vibration from the first pickoff 105 and the second pickoff 105', respectively, are received. A difference between the first pickoff signal and second pickoff signal is calculated in step 720, and a mass flow is determined from the pickoff signal difference in step 725. A velocity, v, is calculated using Equation (7), as an example without limitation, in step 730:

$$m = \rho A v \quad (7)$$

Where:
m is the mass flow rate of the fluid;
ρ is a density of the fluid; and
A is a cross-sectional area of the fluid.

It should be clear that other equations or algorithms, besides Equation (7), are contemplated. Mass flow is directly measured by the flowmeter 5 in step 725, and in step 730, a velocity is derived through Equation (7), after the density is measured. This method provides a diagnostic check to verify a mathematical product of mass and density. In particular, a calculated momentum product term is calculated by multiplying the velocity and the mass flow rate, as indicated in step 735. In step 740, the calculated momentum product term is then compared with the momentum term calculated in step 705. A fault is then indicated in step 745 if the calculated momentum product term deviates from the momentum term to a degree greater than a predetermined threshold.

Figure 8:
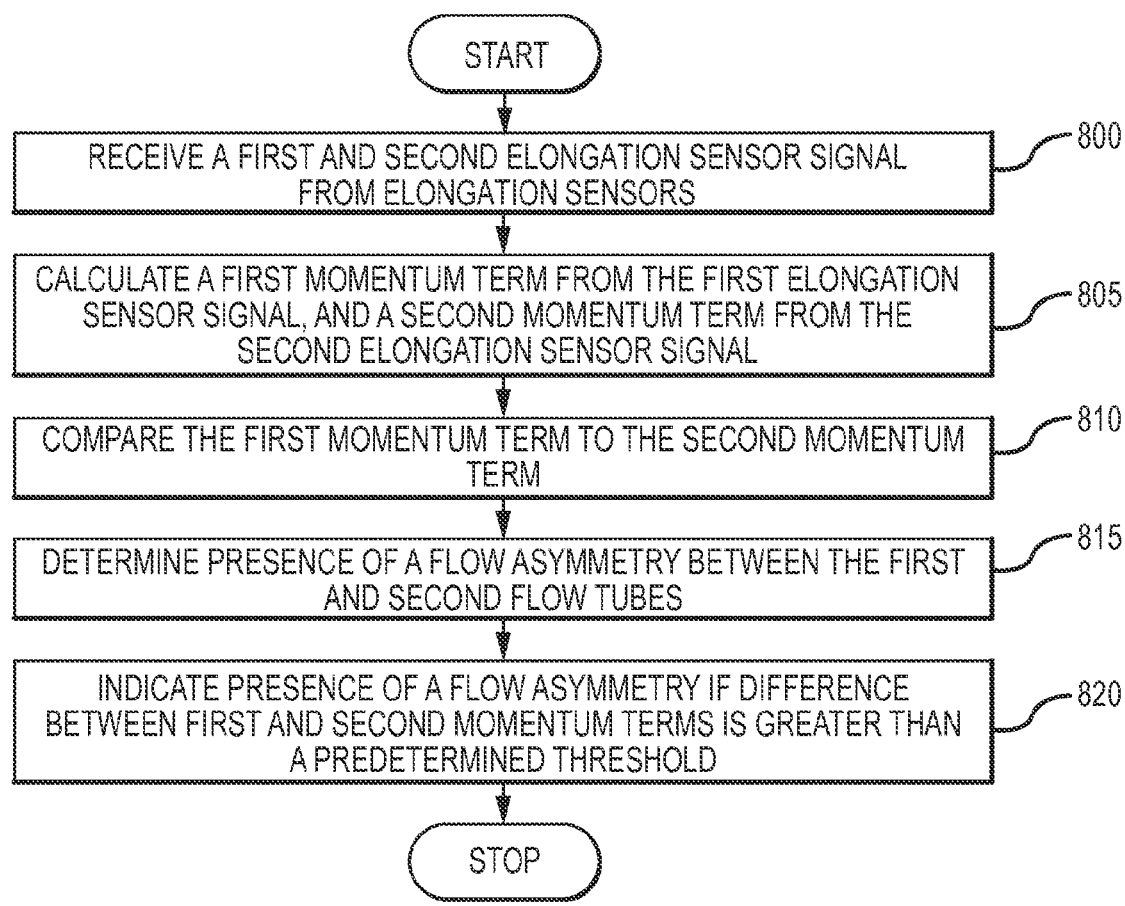
FIG. 8 is a flowchart illustrating an embodiment of a method to calculate flow asymmetry in a flowmeter.

FIG. 8 is a flow chart illustrating a routine performed according to an embodiment, such that a momentum term is utilized to indicate the presence of flow asymmetry between the flow tubes 103, 103' of a flowmeter 5, such as for a flow asymmetry routine 215. A problem with prior art flowmeters is their inherent lack of obstruction or build-up detection. The coil/magnet pickoffs typically utilized measure relative motion, so flow asymmetry is not detectable between flow tubes. Therefore clogs or residue build-up in one of the flow tubes does not interfere with mass flow measurements. It is precisely this "benefit" of coil/magnet sensors that limits their use for detecting clogs or residue build-up in the flow tubes. FIG. 8 outlines an embodiment of a method for determining flow asymmetry, and therefore a potential clog or residue build-up, in flow tubes 103, 103'. In an embodiment, a first elongation sensor 120 is provided with a first flow tube 103, and a second elongation sensor 120 is provided with a second flow tube 103'. Fluid may be provided through the flow tubes 103, 103'. A first and second elongation sensor signal based on vibrational responses to the drive mode vibrations is then received from the first and second elongation sensors 120, respectively, as indicated in step 800. In step 805, a first momentum term from the first elongation sensor signal, and a second momentum term from the second elongation sensor signal are calculated. These values, the first and second momentum terms, are compared to each other in step 810. It is then determined, in step 815, whether a flow asymmetry between the first and second flow tubes 103, 103' is present. The presence of flow asymmetry indicates that there may be a clog or residue build-up on one of the flow tubes 103, 103', since a pair of unobstructed flow tubes should exhibit a symmetrical response. In one embodiment, step 820 is present, wherein the presence of a flow asymmetry is indicated if the difference in the first momentum term and second momentum term is greater than a predetermined threshold.

Figure 9:
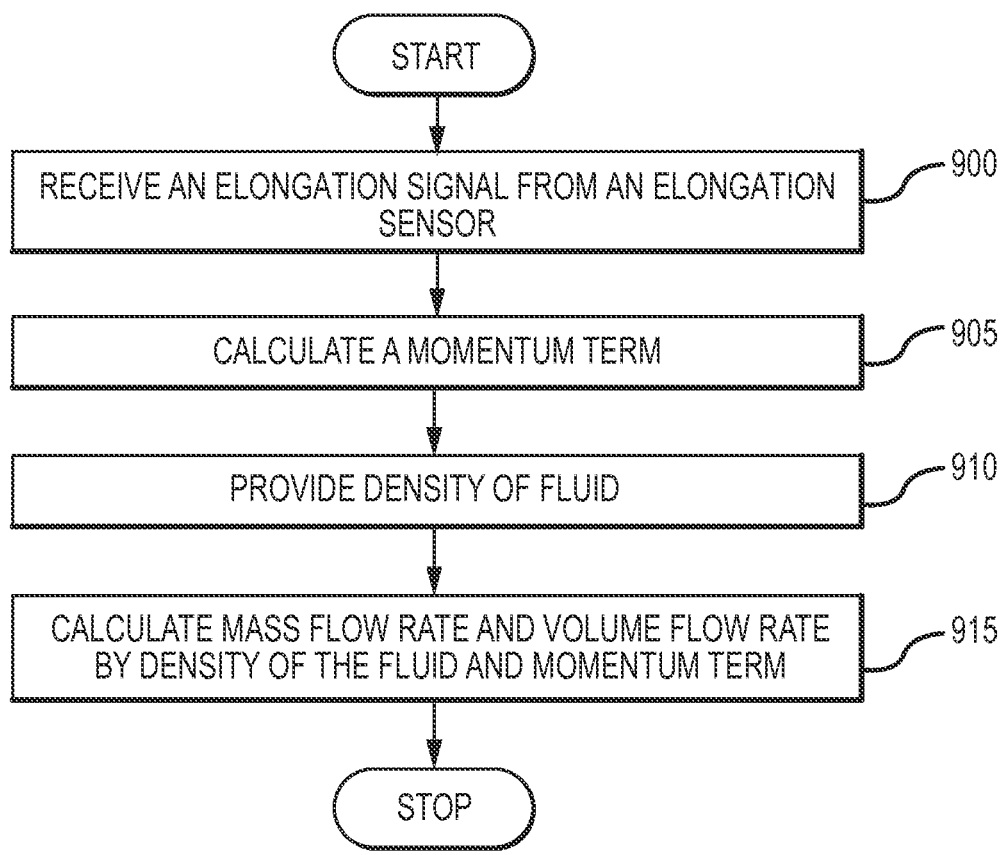
FIG. 9 is a flowchart illustrating an embodiment of a method to calculate a mass flow and volume flow rate.

FIG. 9 is a flow chart illustrating a routine performed according to an embodiment, adapted for meter applications wherein a fluid density (either known or measured) is used in combination with the momentum term to measure and output a mass and volume flow rate. In an embodiment, an elongation sensor 120 is provided on a conduit. Fluid may be introduced and flowed through the conduit, and in step 900 an elongation signal is received from an elongation sensor. A momentum term is calculated in step 905. A density is also provided, either measured or known, in step 910. Lastly, as shown in step 915, the density and momentum term are utilized to calculate mass flow rate and volume flow rate.

Note that for all embodiments disclosed, dedicated elongation sensors, such as strain gages for example, to resolve the momentum term may be placed on the flow tubes 103, 103', independently of the pickoffs 105, 105'. They may be placed at any point along the flow tubes 103, 103'. In the case of strain gages, their orientation on a particular flow tube can be devised to minimize temperature or pressure effects. In one embodiment, a strain gage may be placed in an axial direction, and a second strain gage on the same flow tube could be placed in a circumferential orientation. Depending on how these gages are connected to a bridge circuit, signals within a flow tube or between flow tubes may be cancelled or alternatively magnified, depending on the application. Since the pressure and temperature between flow tubes is generally the same, relative momentum term-derived obstruction detection should be relatively insensitive to such changes, however.

Figure 10:
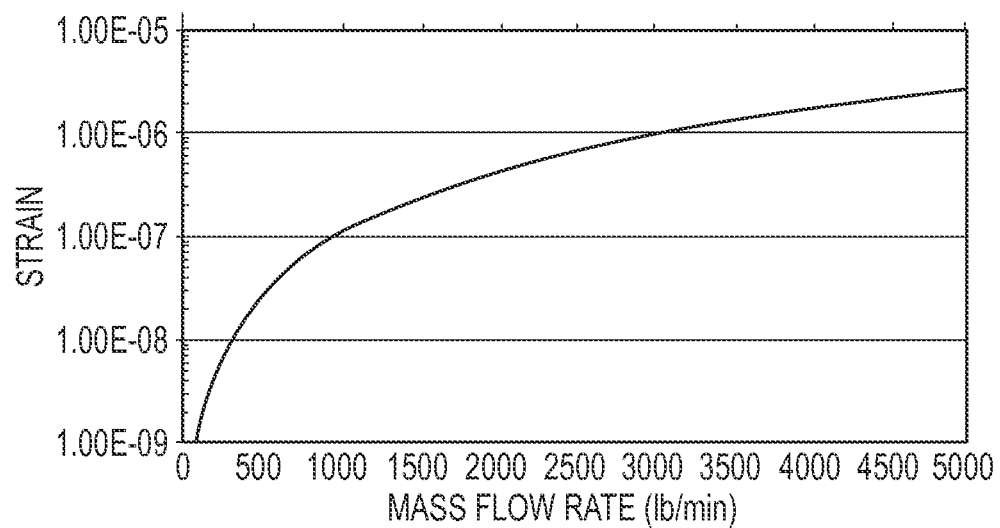
FIG. 10 is a graph illustrating a measured fluid momentum strain vs. mass flow rate in a Coriolis flowmeter.

Turning now to FIG. 10, this graph illustrates a test conducted on a Coriolis mass flowmeter having stainless steel flow tubes. When the flow rate is 0 lb/min, no momentum signal is present. However, as flow rate increases up to 5000 lb/min, the strain measured also increases, thus validating the use of an elongation sensor to detect momentum-induced strain as a viable approach for deriving a momentum term, indicating flow asymmetry, and calculating mass and volume flow rates in non-Coriolis meter implementations.

The detailed descriptions of the above embodiments are not exhaustive descriptions of all embodiments contemplated by the inventors to be within the scope of the invention. Indeed, persons skilled in the art will recognize that certain elements of the above-described embodiments may variously be combined or eliminated to create further embodiments, and such further embodiments fall within the scope and teachings of the invention. It will also be apparent to those of ordinary skill in the art that the above-described embodiments may be combined in whole or in part to create additional embodiments within the scope and teachings of the invention.

Thus, although specific embodiments of, and examples for, the invention are described herein for illustrative purposes, various equivalent modifications are possible within the scope of the invention, as those skilled in the relevant art will recognize. The teachings provided herein can be applied to other devices and methods, and not just to the embodiments described above and shown in the accompanying figures. Accordingly, the scope of the invention should be determined from the following claims.

What is claimed is:

1. A method for determining fluid momentum through one or more conduits, comprising the steps of:
   vibrating at least one of one or more flow tubes in a drive mode vibration;
   receiving an elongation signal from an elongation sensor indicating an elongation of the one or more conduits due to a flowing fluid; and
   calculating a momentum term based on the elongation signal;
   providing a first pickoff and a second pickoff on at least one of the one or more flow tubes;
   receiving a first pickoff signal and second pickoff signal by meter electronics from the first pickoff and the second pickoff, respectively, based on a vibrational response to the drive mode vibration;
   wherein the meter electronics is configured to:
      calculate a difference between the first pickoff signal and second pickoff signal;
      determine a mass flow from the pickoff signal difference;
      calculate a velocity using the mass flow rate;
      calculate a momentum product term by multiplying the velocity and the mass flow rate;
      compare the calculated momentum product term with the momentum term; and
      indicate a fault if the calculated momentum product term deviates from the momentum term to a degree greater than a predetermined threshold.

2. The method for determining fluid momentum through one or more conduits of claim 1, wherein calculating the momentum term comprises the step of deriving the momentum term from an axial strain equation comprising $$\varepsilon_y = \frac{-F_{Ay}}{A_t E} = \frac{+2mv + 2Ap_{avg}}{A_t E},$$

wherein:
   mv is the momentum term;
   $\varepsilon_y$ is the axial strain of the one or more conduits;
   $F_{Ay}$ is an anchor force of the one or more conduits;
   $A_t$ is a cross-sectional area of the one or more conduits;
   E is a modulus of elasticity of the one or more conduits;
   m is a mass flow rate of the fluid;
   v is a fluid velocity of the fluid;
   A is a cross-sectional area of the fluid; and
   $p_{avg}$ is an average static pressure of the fluid.

3. The method for determining fluid momentum through one or more conduits of claim 1, further comprising the steps of:
   receiving a temperature signal from a temperature sensor; and
   calculating a temperature-corrected momentum term.

4. The method for determining fluid momentum through one or more conduits of claim 3, wherein calculating a temperature-corrected momentum term comprises the step of deriving a temperature-corrected momentum term from an axial strain equation comprising wherein:

$$\varepsilon_y = \frac{-F_{Ay}}{A_t E} = \frac{+2mv + 2Ap_{avg}}{A_t E} + \alpha_T \Delta T,$$

$F_{AY}$ is an anchor force;
   mv is the momentum term;
   $\varepsilon_y$ is the axial strain of the one or more conduits;
   $A_t$ is a cross-sectional area of the one or more conduits;
   E is a modulus of elasticity of the one or more conduits;
   m is a mass flow rate of the fluid;
   v is a fluid velocity of the fluid;
   A is a cross-sectional area of the fluid;
   $p_{avg}$ is an average static pressure of the fluid;
   $\alpha_T$ is a coefficient of linear thermal expansion of the one or more conduits; and
   $\Delta T$ is a change in a temperature of the one or more conduits.

5. The method for determining fluid momentum through one or more conduits of claim 1, wherein calculating the velocity, v, comprises m=ρA v, wherein:
   m is the mass flow rate of the fluid;
   ρ is a density of the fluid; and
   A is a cross-sectional area of the fluid.

6. The method for determining fluid momentum through one or more conduits of claim 1, wherein the step of providing an elongation sensor on the one or more conduits proximate a conduit region subjected to momentum re-direction forces, wherein the one or more conduits comprise one or more flow tubes of a vibratory flowmeter, wherein the method comprises the steps of:
   receiving a first and second elongation sensor signal from a first and a second elongation sensors, respectively, based on vibrational responses to the drive mode vibrations;
   calculating a first momentum term from the first elongation sensor signal, and a second momentum term from the second elongation sensor signal;

comparing the first momentum term to the second momentum term; and determining the presence of a flow asymmetry between the first and second flow tubes.

7. The method for determining fluid momentum through one or more conduits of claim 6, further comprising the step of:

indicating a presence of a flow asymmetry if the difference in the first momentum term and second momentum term is greater than a predetermined threshold.

8. The method for determining fluid momentum through one or more conduits of claim 1, comprising the steps of:

calculating a mass flow rate and volume flow rate with a density of the fluid and the momentum term.

9. The method for determining fluid momentum through one or more conduits of claim 8, wherein the step of providing the density of the fluid comprises the step of measuring the density of the fluid.

10. A flowmeter (5) including a sensor assembly (10) and a meter electronics (20), comprising:

one or more flow tubes (103, 103');

a driver (104) coupled to the one or more flow tubes (103, 103') and oriented to induce a drive mode vibration in the one or more flow tubes (103, 103');

at least two pickoffs (105, 105') coupled to the one or more flow tubes (103, 103') and configured to detect the drive mode vibration, wherein the meter electronics (20) is configured to calculate a first momentum term from the drive mode vibration detected by the at least two pickoffs (105,105'); and a first elongation sensor coupled to a first flow tube of the one or more flow tubes and a second elongation sensor coupled to a second flow tube, wherein at least one of the first elongation sensor and the second elongation sensor of the first and second flow tubes is configured to output at least one signal whose amplitude is proportional to a fluid momentum-induced strain of the one or more flow tubes (103, 103'), and wherein the meter electronics (20) is configured to calculate a second momentum term from the signal, wherein the meter electronics (20) is configured to determine there is a fault in the flowmeter (5) if the first momentum term deviates from the second momentum term to a degree greater than a threshold.

11. The flowmeter (5) including a sensor assembly (10) and a meter electronics (20) of claim 10, wherein the momentum term is derived from an axial strain equation comprising $$\varepsilon_y = \frac{-F_{Ay}}{A_t E} = \frac{+2mv + 2Ap_{avg}}{A_t E},$$

wherein:

mv is the momentum term;
$\varepsilon_y$ is the axial strain of the conduit;
$F_{Ay}$ is an anchor force of the conduit;
$A_t$ is a cross-sectional area of the conduit;
E is a modulus of elasticity of the conduit;
m is a mass flow rate of the fluid;
v is a fluid velocity of the fluid;
A is a cross-sectional area of the fluid; and
$p_{avg}$ is an average static pressure of the fluid.

12. The flowmeter (5) including a sensor assembly (10) and a meter electronics (20) of claim 10, comprising at least one temperature sensor (106) coupled to the one or more flow tubes (103,103'), wherein the meter electronics (20) is configured to calculate a temperature-corrected momentum term, wherein the temperature-corrected momentum is derived from an axial strain equation comprising $$\varepsilon_y = \frac{-F_{Ay}}{A_t E} = \frac{+2mv + 2Ap_{avg}}{A_t E} + \alpha_T \Delta T,$$

wherein:

$F_{Ay}$ is an anchor force;
mv is the momentum term;
$\varepsilon_y$ is the axial strain of the conduit;
$A_t$ is a cross-sectional area of the conduit;
E is a modulus of elasticity of the conduit;
m is a mass flow rate of the fluid;
v is a fluid velocity of the fluid;
A is a cross-sectional area of the fluid;
$p_{avg}$ is an average static pressure of the fluid;
$\alpha_T$ is a coefficient of linear thermal expansion of the conduit; and
$\Delta T$ is a change in the conduit temperature.

13. The flowmeter (5) including a sensor assembly (10) and a meter electronics (20) of claim 10, wherein the elongation sensor (120) comprises at least one of a strain gage, an optical sensor, and a laser.

14. The flowmeter (5) including a sensor assembly (10) and a meter electronics (20) of claim 10, wherein the signal is a resistance having an amplitude proportional to the fluid momentum-induced strain.

* * * * *